(12) United States Patent
Hornof

(10) Patent No.: US 9,597,277 B2
(45) Date of Patent: Mar. 21, 2017

(54) USE OF POLYMERS

(75) Inventor: Margit Hornof, Vienna (AT)

(73) Assignee: CROMA-PHARMA GESELLSCHAFT M.B.H., Leobendorf (AT)

(*) Notice: Subject to any disclaimer, the term of this patent is extended or adjusted under 35 U.S.C. 154(b) by 791 days.

(21) Appl. No.: 12/520,820

(22) PCT Filed: Dec. 21, 2007

(86) PCT No.: PCT/AT2007/000585
§ 371 (c)(1),
(2), (4) Date: Jun. 22, 2009

(87) PCT Pub. No.: WO2008/077172
PCT Pub. Date: Jul. 3, 2008

(65) Prior Publication Data
US 2010/0028399 A1 Feb. 4, 2010

Related U.S. Application Data

(60) Provisional application No. 60/871,534, filed on Dec. 22, 2006.

(30) Foreign Application Priority Data

Dec. 22, 2006 (AT) ................. A 2136/2006

(51) Int. Cl.
| | |
|---|---|
| A61F 13/00 | (2006.01) |
| A61K 8/73 | (2006.01) |
| A61L 26/00 | (2006.01) |
| A61L 27/20 | (2006.01) |
| A61L 27/52 | (2006.01) |
| A61L 27/54 | (2006.01) |
| A61L 27/60 | (2006.01) |
| A61Q 19/08 | (2006.01) |

(52) U.S. Cl.
CPC ............ *A61K 8/735* (2013.01); *A61L 26/008* (2013.01); *A61L 26/0023* (2013.01); *A61L 27/20* (2013.01); *A61L 27/52* (2013.01); *A61L 27/54* (2013.01); *A61L 27/60* (2013.01); *A61Q 19/08* (2013.01); *A61K 2800/522* (2013.01); *A61K 2800/91* (2013.01); *A61L 2300/40* (2013.01)

(58) Field of Classification Search
CPC ...... A61K 8/735; A61K 27/52; A61L 26/0023
See application file for complete search history.

(56) References Cited

U.S. PATENT DOCUMENTS

| | | | | |
|---|---|---|---|---|
| 4,713,448 A | | 12/1987 | Balazs et al. ................. | 536/55.1 |
| 5,785,642 A | | 7/1998 | Wallace et al. ................ | 600/30 |
| 7,053,068 B2 | * | 5/2006 | Prinz ............................ | 514/55 |
| 2004/0219217 A1 | * | 11/2004 | Volpato et al. ............... | 424/488 |
| 2005/0222083 A1 | * | 10/2005 | Bulpitt et al. ................. | 514/54 |
| 2005/0282747 A1 | * | 12/2005 | Clark et al. ................... | 514/12 |
| 2007/0087059 A1 | * | 4/2007 | Everaerts et al. ............ | 424/484 |

FOREIGN PATENT DOCUMENTS

| | | |
|---|---|---|
| EP | 0 161 887 | 11/1985 |
| WO | WO 96/15810 | 5/1996 |
| WO | WO 99/31167 | 6/1999 |
| WO | WO 00/16818 | 3/2000 |
| WO | WO 0016818 * | 3/2000 |
| WO | WO 03/020771 | 3/2003 |
| WO | WO 03/080135 | 10/2003 |
| WO | WO 2004/037164 | 5/2004 |
| WO | WO 2004/073759 | 9/2004 |
| WO | WO 2006/008270 | 1/2006 |
| WO | WO 2006/056204 | 6/2006 |

OTHER PUBLICATIONS

European Examination Report, issued in European Application No. 07 855 366.6-1219, mailed Jan. 15, 2010.
Agren et al., "Reactive oxygen species contribute to epidermal hyaluronan catabolism in human skin organ culture," *Free Radic. Biol. Med.*, 23:996-1001, 1997.
Aruoma and Halliwell, "The iron-binding and hydroxyl radical scavenging action of anti-inflammatory drugs," *Xenobiotica.*, 18:459-470, 1988.
Bernkop-Schnürch, "Thiomers: a new generation of mucoadhesive polymers," *Adv. Drug Deliv. Rev.*, 57:1569-1582, 2005.
Bernkop-Schnürch et al., "Thiolated chitosans," *Eur. J. Pharm. Biopharm.*, 57:9-17, 2004.
Halliwell et al., "The characterization of antioxidants," *Food Chem. Toxicol.*, 33:601-617, 1995.
Hornof et al., "Mucoadhesive ocular insert based on thilated poly(acrylic acid): development and in vivo evaluation in humans," *J. Controlled Release*, 89:419-428, 2003.
Lee et al., "Thiolated chitosan nanparticles enhance anti-inflammatory effects of intranasally delivered theophylline," *Respiratory Research*, 7:112, 2006.
Lemperle et al., "Avoiding and treating dermal filler complications," *Plast. Reconstr. Surg.*, 118:92S-107S, 2006.
Lepperdinger et al., In: *Chemistry and Biology of Hyaluronan*, pp. 71-82, 2004.
Parada et al., "A histologic study of adverse effects of different cosmetic skin fillers," *Skinmed*, 4:345-349, 2005.
Rose et al., "Ocular oxidants and antioxidant protection," *Proc. Soc. Exp. Biol. Med.*, 217:397-407, 1998.
Sakurai et al., "Anti-inflammatory activity of superoxide dismutase conjugated with sodium hyaluronate," *Glycoconj. J.*, 14:723-728, 1997.
Shu et al., "Disulfide cross-linked hyaluronan hydrogels," *Biomacromolecules*, pp. 1304-1311, 2002.

* cited by examiner

Primary Examiner — Snigdha Maewall
(74) Attorney, Agent, or Firm — Norton Rose Fulbright US LLP

(57) ABSTRACT

The present invention relates to the use of a thiol-group-containing polymer for preparing an implant for tissue augmentation, wherein the basis polymer is a polysaccharide.

19 Claims, 2 Drawing Sheets

USE OF POLYMERS

This application is a national phase application under 35 U.S.C. §371 of International Application No. PCT/AT2007/000585 filed 21 Dec. 2007, which claims priority to Austrian Application No. A 2136/2006 filed 22 Dec. 2006 and U.S. Provisional Application No. 60/871,534 filed 22 Dec. 2006. The entire text of each of the above-referenced disclosures is specifically incorporated herein by reference without disclaimer.

The invention relates to the use of polymers for tissue augmentation for medical and cosmetic reasons.

For the augmentation of tissues, polymers like e.g. hyaluronic acid crosslinked with ether and ester compounds (crosslinked with divinyl sulfone: WO 2006/056204; crosslinking with aldehydes: U.S. Pat. No. 4,713,448; crosslinked with multifunctional epoxy compounds: EP 0 161 887) are usually used. After implantation into the human body these compounds may lead to inflammatory reactions, allergic reactions and foreign body reactions (Parade et al. Skinmed. 4 (2005): 345-349; Lemperle et al. Plast. Reconstr. Surg. 118 (2006): 92S-107S). Such inflammatory processes may lead to the development of reactive oxygen compounds.

The activation of oxygen to reactive oxygen compounds (free radicals and non-radical oxygen species) is part of the normal metabolic processes within the framework of cellular processes, auto-oxidation reactions and enzymatic reactions. Further causes for the formation of reactive oxygen compounds are, e.g., inflammatory processes, joint and tissue injuries as well as exogenic environmental factors, such as UV radiation, cigarette smoke, radiation exposure and ozone. Normally, there exists a balance between oxidative and reductive processes. If, however, the oxidative reactions prevail, an oxidative stress (oxidative condition) will develop. By the attack of the free radicals, lipids, proteins and DNA become damaged. This damage is, i.a., probably the cause of age-related changes and diseases, e.g. of the aging of skin, diabetes, vascular diseases and neurodegenerative diseases.

Free radicals, such as hydroxyl radicals, in many cases are co-responsible for inflammatory diseases, e.g. for the development and perpetuation of inflammatory diseases of the joints, such as rheumatoid arthritis. Within the setting of an arthrosis, free radicals will cause the degradation of hyaluronic acid in the synovial fluid, leading to a decrease in the viscosity and in the lubricating effect of the synovial fluid (Lepperdinger et al. in Chemistry and Biology of Hyaluronan (2004): 71-82).

Normally, also the tear fluid contains radical scavengers, such as, e.g., cysteine, ascorbic acid and reduced glutathione, and antioxidant enzymes, such as, e.g., lactoferrin and lysozyme, so as to protect the eye surface against oxidative damage by free radicals (hydroxyl radicals, e.g.) (Rose et al., Proc. Soc. Exp. Biol. Med. 217 (1998): 397-407).

By the removal of free radicals by means of radical scavengers, inflammatory processes can be inhibited. Endogenous protective functions against reactive oxygen compounds are carried out by enzymes, such as catalase, superoxide dismutase (SOD) and glutathione peroxidase (GPx), as well as reduced glutathione (GSH) and iron and copper forming proteins (e.g. ferritin, albumin, lactoferrin). Important exogenous antioxidants are ascorbic acid and derivatives, tocopherole and retinoids. Most of the anti-inflammatory low-molecular medicaments, such as, e.g., Diclofenac and Piroxicam, also have radical-scavenging properties (Aruoma and Halliwell, Xenobiotica 18 (1988): 459-470).

Hyaluronic acid, which is used often for tissue augmentation, exhibits itself a minor anti-inflammatory effect and is a weak scavenger of hydroxy radicals. In order to increase the anti-oxidative effect of hyaluronic acid and to reduce inflammatory reactions after the injection of hyaluronic acid the combined application of hyaluronic acid with mannitol has been proposed (WO 2004/073759). However this kind of application is disadvantageous because mannitol may diffuse out of the hyaluronic acid depot. In a further approach the enzyme superoxide dimutase was conjugated to hyluronic acid which resulted in a decrease of enzyme activity of 30% (Sakurai et al. Glycoconj J. 14 (1997): 723-728). Although both proposals increase the antioxidative effect of hyaluronic acid, the desired effect lasts for a short period of time, because the resorption of the hyaluronic acid is not slowed down. Unmodified hyaluronic acid, i.e. not crosslinked hyaluronic acid, is resorbed within a couple of hours or days after its implantation into the human body.

Therefore it is an object of the present invention to provide compounds for tissue augmentation which, on account of their radical-scavenging and multivalent metal ion-complexing properties have an antioxidant effect and simultaneously are characterized by a longer dwell time at the site of application.

Therefore, the present invention relates to the use of a thiol-group-containing polymer for producing an implant for the augmentation and stabilisation of tissue, wherein the polymer is a polysaccharide, which is preferably bio-degradable. The application occurs preferably via subdermal, intradermal, subcutaneous or intramuscular injection.

It has been found that thiol-group-containing polymers, i.e. thiol-group-containing, physiologically tolerable polymer compounds, are particularly well suited for tissue augmentation, wherein these polymers exhibit at the same time an anti-inflammatory/antioxidative protective effect.

Oxidative processes play a decisive role in a large number of diseases, since such processes lead to a damage of DNA, proteins and lipids. The oxidative processes may be induced by extrinsic causes (e.g. by environmental influences, such as radiation (UV radiation, ionizing radiation), oxidating agents etc.), and intrinsic causes (e.g. by inflammations), respectively.

Direct coupling of thiol antioxidants to the polymer has the advantage that the antioxidative protective effect is maintained during the whole dwell time of the polymer and that the crosslinking due to the functions of disulfide bonds contributes to the stability of the polymer. The improvement of the hydroxy scavenger and anti-oxidative properties of hyaluronic acid achieved by thiolation is exemplified in FIG. 2, FIG. 3 and FIG. 4.

According to the present invention the term "implant" relates to an injectable, preferable sterile, fluid, gel-like or semi solid preparation, which will essentially stay for at least several weeks to month or even for years at or in the vicinity of the site of application until the implant is degraded at least partially, preferably substantially completely.

According to a preferred embodiment, the thiol-group-containing polymer has a molecular mass of at least 10000 g/mol, preferably of at least 25000 g/mol, in particular at least 50000 g/mol.

The molecular mass of the inventive thiol-group containing polymer is of particular relevance if it is important that, when using the polymer, the latter will remain directly at the active site or in the immediate vicinity thereof for a longer period of time than antioxidants known so far which have a substantially lower molecular mass. This is particularly advantageous if it is important to control local oxidation processes or to stop them, respectively, or to reduce them. Therefore, it is preferred for the thiol-group-containing polymer to have at least a molecular mass of 10000 g/mol.

The thiol-groups within the polymer preferably form inter- and/or intra-molecular disulfide bonds.

The ability of the inventive thiol-group-containing polymer to form disulfide bonds is necessary if it is important to exert the antioxidant properties at the active site or in the vicinity thereof. As illustrated in FIG. 1, the reduced thiol-group-containing polymer may be used for reducing glutathion disulfide which plays a decisive role in the detoxification of hydrogen peroxide. Due to their antioxidant properties, thiol-group-containing polymers furthermore inhibit the oxidative stress directly caused by the hydroxyl radicals and, thus, they can prevent damage of the DNA, lipids and proteins. Furthermore, thiol-group-containing polymers inhibit the formation of hydroxyl radicals by complexing divalent iron ions. In this way, the Fenton reaction of hydrogen peroxide to hydroxyl radicals can be stopped or largely reduced, respectively.

After the synthesis of the polymer according to the present invention all its thiol-groups are preferably available as free thiol-groups, so that the polymer is crosslinked in a low degree or even not crosslinked at all. This allows to produce single phase aqueous solutions of polymers which can easily be further processed and allows to introduce into said polymers pharmaceutical excipients or pharmaceutically active compounds. The crosslinking occurs afterwards under controlled conditions by changing the pH to physiological pH values between pH 6-10.5 in the presence of oxygen. The addition of a crosslinking agent is not necessary. For the application in tissue augmentation for medicinal and cosmetic reasons the partial crosslinking of the polymers via disulfide bridges is preferred.

It could be shown also that polymers comprising thiol-groups crosslinked via disulfide bridges for tissue augmentation exhibit a much higher stability compared to conventional polymers known in the art The polymer according to the present invention can be used cosmetically or therapeutically whereby soft tissue, in particular dermal tissue, muscle tissue and connective tissue, is preferably augmented. Cosmetic dermal augmentation is preferably used to treat-cosmetically deep wrinkles in the face region, in particular in nasolabial folds, upper lips folds and forehead folds, fine folds in the eye and cheek region, small skin unevenness and building up cheeks of shrunken cheeks.

The thiol-group portion of the polymer preferably is more than 20 μmol/g of polymer, preferably more than 50 μmol/g of polymer, in particular more than 100 μmol/g of polymer.

The antioxidant properties of the inventive thiol-group-containing polymers are particularly advantageous if the polymer comprises at least 50 μmol of thiol-groups per gram of polymer.

According to the invention, polymers which are physiologically tolerable and which can be modified by thiol-groups are suitable. Basis polymers are selected from the group of polysaccharides. Thiol-group-containing polymers are preferably selected from the group consisting of thiol-group containing hyaluronic acid, thiol-group containing chitosan and combinations of these thiol-group-containing polymers have proved to be particularly advantageous for the use according to the invention.

Some of these polymers, such as, e.g., thiolated hyaluronic acid, are already being used as excipients in medicaments, e.g. so as to introduce active substances more easily and efficiently in mucus layers (cf. e.g. WO 00/25823). Now, however, it has surprisingly been found that such polymer compounds themselves exhibit a pharmacologic effect and may be used as antioxidants. The thiol-groups of the polymers are capable of significantly increase the antioxidant properties possibly present in non-thiolated polymers, or to impart antioxidant properties to the polymers.

The dwell time can be influenced by the choice of the polymer. The biopolymers hyaluronic acid and chitosan are degraded by hyaluronidase and lysozyme, respectively, naturally present in a mammal, in particular in a human. For the degradation of synthetic polymers like polyacrylic acid or polyacrylamide no enzymes are present in a mammal body which has the consequence that said polymers have to be removed from the body by surgery, whereby bio-degradable polymers over a time period of at least 6, 12, 24 or even 60 months are degraded by enzymes and consequently removed from the body.

The at least one thiol-group of the inventively used polymer preferably is derived from a physiologically tolerable thiol compound, e.g. cysteine, cysteamine and N-acetyl-cysteine, which means that these thiol compounds or their derivatives can be used to thiolate polymers.

According to the invention, the thiolation can be effected by all kinds of chemical reactions by which thiol compounds are bound to polymers, in particular to water-soluble polymers. For several reasons, the use of cysteine and cysteine derivatives is advisable for the thiolation, since the former are physiologically tolerable, on the one hand, and easy and cheap to obtain, on the other hand. Cysteine and cysteine derivatives preferably can be bound to the polymer via an amide bond. On the other hand, the inventive polymer may also be prepared in that in the course of the production of the polymer, at least one monomer is (co-)polymerized with thiol-groups, which has free thiol-groups in the polymer, which means that the thiol-groups are not directly reacted in the polymerizing reaction. Such a polymer which contains at least one monomer which has free thiol-groups in the polymer is also preferred according to the invention (cf. e.g. Bernkop-Schnürch, Adv. Drug Deliv. Rev. 57 (2005): 1569-1582).

Depending on the site of application or active site, the implant of the invention is provided in a corresponding formulation. The auxiliary substances required therein will each depend on the formulation and are sufficiently known to the person skilled in the art (cf. e.g. Sarfaraz Niazi, "Handbook of Pharmaceutical Manufacturing Formulations", CRC Press (2004)).

The thiol-group-containing polymers according to the invention may also be used subcutaneously and intradermally for dermal augmentation. In cosmetics, polymers such as, e.g., hyaluronic acid, are known and frequently used auxiliary agents for alleviating signs of skin aging (wrinkles, dryness, loss of elasticity) which, i.a., are associated with a reduction of hyaluronic acid by free radicals in the tissue (Agren et al., Free Radic. Biol. Med. 23 (1997): 996-1001). Due to the antioxidant properties of the inventive thiol-group-containing polymers, preferably thiol-group containing hyaluronic acid, the radical-mediated degradation of thiol-group-containing hyaluronic acid slows down after a subcutaneous or intradermal application.

In the formulations for subcutaneous or intradermal application, the thiol-group-containing polymer may be present at a concentration of from 0.001-20% (m/v), preferably of from 0.01-10% (m/v). The formulations may, moreover, contain additional excipients which are normally used for preparations for subcutaneous or intradermal application, e.g. buffer salts, stabilizers, excipients for adjusting the desired osmolality, excipients for adjusting the desired viscosity, and excipients for enhancing the tolerance of the formulation. The osmolality and the pH of the finished formulation preferably are in the physiologic range.

The implant is particularly preferred formulated as gel or as aqueous, preferably single phase, preparation.

The implant according to the invention which comprises at least one thiol-group-containing polymer can be formulated in a plurality of application forms. Particularly advantageous is the provision of the formulation as aqueous solution/preparation. If the implant is provided as an aqueous solution, the latter may be administered in a simple manner subcutaneously, intradermally or intramuscularly at a desired location.

The use of polymers having the form of gels and aqueous low-viscous solutions, or in the form of solid preparations (also as inserts for the controlled active substance release) as implants in the human body may cause inflammatory reactions in the surrounding tissue. By the radical-scavenging and antioxidant effect which the inventive thiol-group-containing polymers exert, these inflammatory reactions can be alleviated or entirely eliminated, respectively. This applies, e.g., to the intradermal and subcutaneous application of thiol-group-containing polymers for injection underneath wrinkles, to the use of thiol-group-containing polymers for sphincter augmentation and to the implantation of (semi-) solid preparations based on thiol-group-containing polymers.

It turned out that it is particularly advantageous to use the polymer according to the present invention as a homogenous single phase aqueous preparation which can be distributed after the application in an easy way and which can be degraded equally slowly by enzymes present at the site of application. With crosslinked polymer particles as disclosed, for instance, in the WO 99/31167 only two-phase formulations can be produced which consist of a suspension of particles in a liquid carrier medium. With such formulations it is difficult to estimate the required amount of the implant for an augmentation (e.g. injections underneath wrinkles), because the carrier medium is absorbed rather quickly from the body and the residual particles have a significantly reduced volume. Therefore, the application has to be corrected which makes it difficult to obtain a satisfying result.

According to a preferred embodiment, the medicament or the implant furthermore additionally comprises at least one active substance; for the application in dermatology, preferably an active substance from the group of the local anesthetics (e.g. lidocaine, prilocaine, procaine, mepivacaine), antimycotics (e.g. omoconazole, clotrimazole, bifonazole, miconazole, floconazole, itraconazole, oxiconazole, fenticonazole, terbinafine, ciclopirox, amorolfine), antihistamines, antiallergic agents, anti-inflammatory agents, antibiotics (e.g. tetracyclin and derivatives, fusidinic acid, chloramphenicol, neomycin, bacitracin, gentamicin, tyrothricin, mupirocin, virginiamycin, rifaximin and amicacin), chemotherapeutic agents, antiviral agents, emollients, skin-protecting agents, agents for treating wounds, topical anti-acne agents and corticosteroids, non-steroidal antiphlogistics, agent for treating hemorrhoids, topical antiseptics and iodine-containing agents. In addition, at least one pharmaceutical excipient from the group of the buffer salts, preserving agents, excipients for adjusting the desired osmolality, excipients for adjusting the desired viscosity, stabilizers, softeners, coating materials, flow agents, binders, lubricants, fillers, desiccants, disintegrating agents, solvents, solubilizers and excipients for increasing the tolerance of the formulation, may be contained in the implant.

Besides the inventive thiol-group-containing polymers and the possibly admixed excipients required or of advantage for particular formulations, the medicament, or implant, respectively, may comprise further active substances. Active substances, which preferably are admixed to the thiol-group-containing polymer, may themselves have antioxidant properties or may serve to heal, alleviate or prevent the antioxidant disease or the disease caused by oxidative stress, respectively. Anti-inflammatory substances and vitamins having antioxidant activity shall be mentioned by way of example in this context.

According to a preferred embodiment of the present invention, the implant additionally comprises at least one unmodified polymer. In implants which comprise both thiol-group-containing polymers and also unmodified polymers, their mixing ratio relative to each other is variable. According to the invention, under "unmodified polymers" polymers are summarized which are entirely unmodified, or which are modified, yet do not have any thiol-group, respectively.

According to a preferred embodiment of the present invention, the implant comprises the thiol-group-containing polymer at a concentration of from 0.001 to 100% by weight, preferably of from 0.01 to 90% by weight, even more preferred of from 0.05 to 80% by weight; wherein the administration occurs more preferably at a concentration of 0.1 to 20%, or even most preferably of 0.1 to 10%.

The implant according to the invention may either entirely consist of thiol-group-containing polymer, or it may be mixed with excipients, carriers and pharmaceutically active substances.

Due to the thiol-groups contained in the polymer of the invention, the polymer has antioxidant properties.

According to a preferred embodiment of the present invention the tissue to be augmented is selected from the group consisting of dermal tissue, muscle tissue and connective tissue.

A further aspect of the present invention relates to an implant for tissue augmentation comprising at least one thiol-group-containing polymer as defined above.

Yet a further aspect of the present invention relates to a method for the cosmetic treatment of skin, and for reducing and/or preventing the aging of skin, in which a thiol-group-containing polymer as defined above is applied subcutaneously and/or intradermally.

Thiol-group-containing polymers may be used for the cosmetic treatment of the skin and for reducing aging of the skin. Polymers, such as, e.g., hyaluronic acid, are auxiliary agents well known and frequently used in cosmetics, e.g. for injection underneath wrinkles and into lips. For this purpose, mostly a viscous gel of long-chain molecules is used which is very slowly degraded by the body. In a further process, the polymers are broken up with UV light, massaged into the skin, and subsequently laser-treated, whereby the massaged-in polymer fragments again react to macromolecules in the skin. Such polymers are used as an alternative to collagen.

The cosmetic use of polymers, particularly of hyaluronic acid, may result in partially pronounced side effects, such as, e.g., skin rash and reddening based on oxidative stress. It has now been found out that when administering thiol-group-containing polymers, such side effects can be entirely prevented, or largely reduced, respectively.

The invention will be explained in more detail by way of the following examples and figures to which, of course, it is not restricted.

EXAMPLES

Example 1

Inhibition of the Oxidating Effect of Hydroxyl Radicals by Inventive Thiol-Group-Containing Polymers The hydroxyl radical-scavenging properties of the inventive thiol-group-containing polymers were evaluated with the deoxyribose test (Halliwell et al., Food Chem. Toxicol. 33 (1995): 601-617). In this test system, hydroxyl radicals are generated by iron ions which attack deoxyribose. The resultant degradation products react with thiobarbituric acid to a pink colouring agent whose absorption is measured. With this method, both the radical-scavenging and also the complexing properties of the inventive thiol-group-containing polymers are tested.

The hydroxyl radical-scavenging and complexing properties of the inventive thiol-group-containing polymers were also evaluated with the deoxyribose test in dependence on their concentration and their degree of modification. It is important that the inventive thiol-group-containing polymers still unfold their antioxidant activity even at low concentrations because in this way—in combination with the extended dwell time of these thiol-group-containing polymers—a long-lasting effect can be achieved. Moreover, in preparations for ocular, intra-articular, intradermal or subcutaneous applications, high-molecular polymeric compounds can be used only at relatively low initial concentrations, since otherwise, due to their high viscosity, an optimum tolerance is no longer ensured.

For this test, polymer solutions were freshly prepared by dissolving the polymer in phosphate buffer, pH 7.4, so that the final concentration of the polymer in the entire sample solution was 0.1% (m/v). If necessary, the pH of the sample solution was adjusted to 7.4 by the addition of NaOH.

Phosphate buffer, pH 7.4 without polymer served as the control. To 0.6 ml of the sample solution, at first 0.1 ml of a 10 mM 2-deoxy-D-ribose solution were added.

Immediately after the addition of 0.1 ml of a freshly prepared 10 mM FeSO$_4$ solution, the samples were incubated for 120 min at 37° C. The reaction was stopped by the addition of 0.5 ml of 2.5% (v/v) trifluoroacetic acid. After the addition of 0.2 ml of 1% (m/v) thiobarbituric acid, the samples were incubated for 20 min at 95° C. for color development. Then the samples were cooled to room temperature and centrifuged for 5 min. One aliquot of the sample solution was transferred in microphotometric cuvettesi and the absorption was measured at 532 nm.

The antioxidant properties of the inventive polymer were calculated in the form of the inhibition of the deoxyribose oxidation:

$$\text{Oxidation inhibition in \%} = (1 - (A_s/A_c)) \cdot 100,$$

wherein $A_s$ is the absorption of the sample, and $A_c$ is the absorption of the control.

Figure 1:
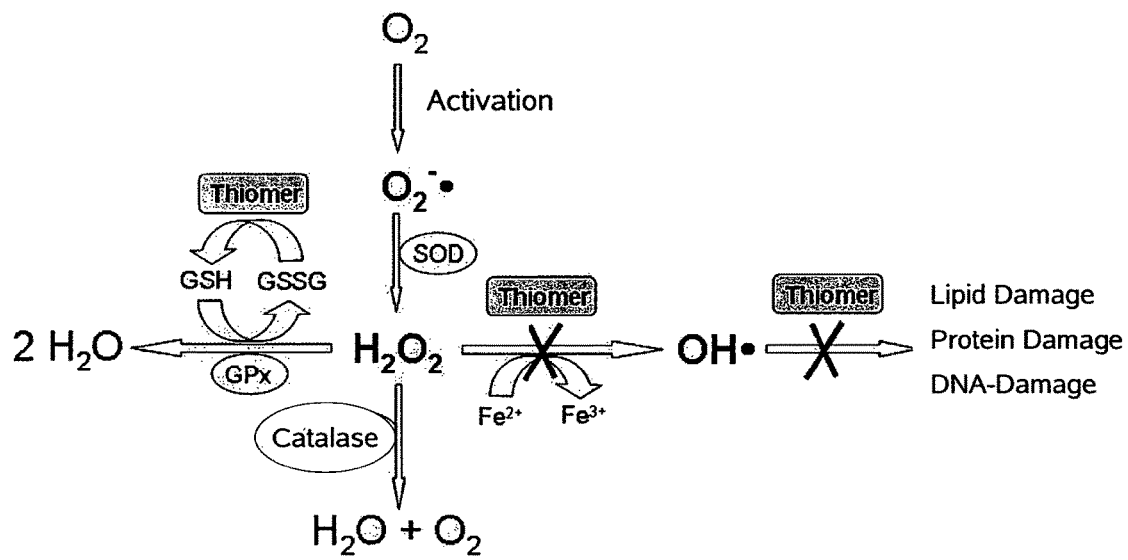
FIG. 1 shows a schematic representation of the antioxidant active mechanism of the thiol-group-containing polymers.
Figure 2:
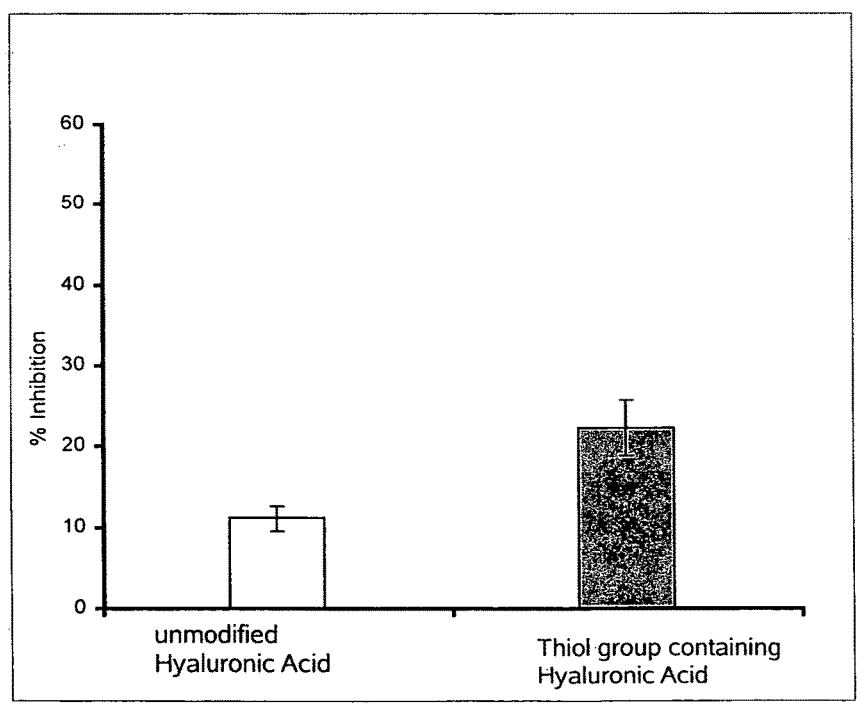
FIG. 2 shows the inhibition of the oxidating effect of hydroxyl radicals by 0.1% (m/v) aqueous solutions of thiolated hyaluronic acid in comparison with the unmodified polymers (n≥3; ±SD).
Figure 3:
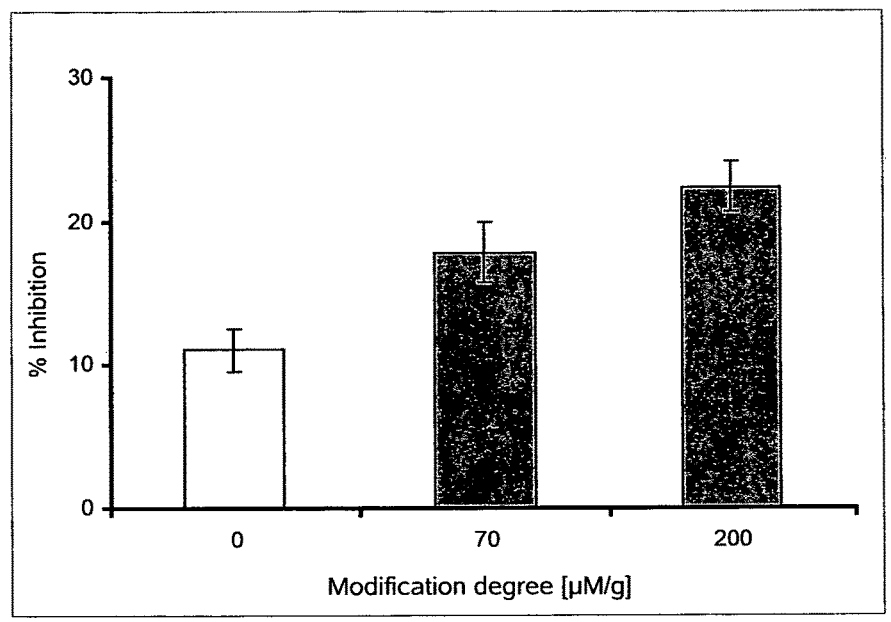
FIG. 3 shows the inhibition of the oxidating effect of hydroxyl radicals by 0.1% (m/v) aqueous solutions of thiolated hyaluronic acid, modified to various degrees (200 μM of thiol-groups/g of polymer and 70 μM of thiol-groups/g of polymer) in comparison with unmodified hyaluronic acid (n≥4; ±SD).
Figure 4:
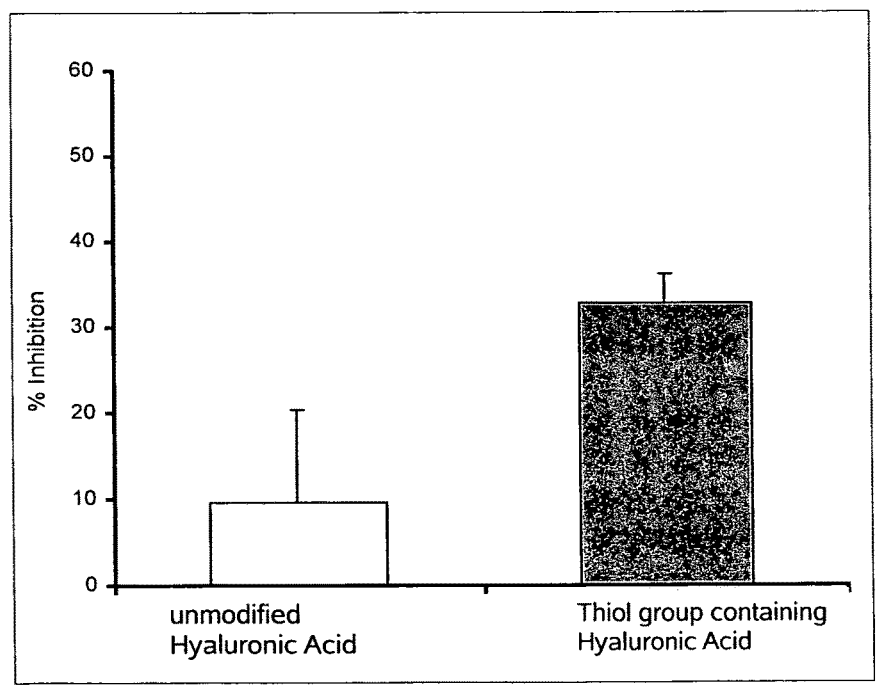
FIG. 4 shows the inhibition of the lipid oxidation on porcine cornea in vitro by 0.1% (m/v) aqueous solutions of thiolated hyaluronic acid in comparison with unmodified polymers (n≥3; ±SD).

The results are illustrated in FIGS. 2 and 3. On the y-axis, in each case the inhibition of the oxidation effect (in %) of hydroxyl radicals by the polymers is illustrated. The values illustrated are the mean values of at least 3 test repetitions±standard deviation. In FIG. 2 it is shown that by the covalent binding of thiol compounds, the antioxidant effect of hyaluronic acid could be significantly increased. The dependence of the antioxidant effect of the polymers according to the invention on the degree of modification with thiol compounds is illustrated in FIG. 3 by way of the example of thiolated hyaluronic acid. Thiolated hyaluronic acid having a degree of modification of 200 μM of thiol-groups/g of polymer thus has a higher antioxidant effect than thiolated hyaluronic acid having a degree of modification of 70 μM of thiol-groups/g of polymer.

Example 2

Inhibition of the Lipid Peroxidation in the Skin by Thiol-Group-Containinq Polymers With an in vitro-test, the potential of the thiol-group-containing polymers to inhibit the oxidation of lipids of the dermis was evaluated. Peroxidation of intracellular lipids caused e.g. by UU radiation leads to damages of the human skin/dermis.

With this method, both the radical-scavenging and the complexing properties of the thiol-group-containing polymers are tested (Halliwell et al., Food Chem. Toxicol. 33 (1995): 601-617). In this in vitro-test system, the lipid peroxidation is accelerated by the addition of iron ions and heating. The oxidated lipid fragments (TBARS; thiobarbituric acid reactive substances) react with thiobarbituric acid to a pink coloring agent whose absorption is measured.

Polymer solutions are freshly prepared in isotonic phosphate buffer so that the final concentration of the polymer in the entire sample solution was 0.05% (m/v). The pH of the sample solutions was adjusted to 7.4 by the addition of NaOH. Isotonic phosphate buffer, pH 7.4 served as the control. To these samples, 100 mg of porcine dermis were added. After the addition of 0.3 ml of a freshly prepared 20 mM FeSO$_4$ solution, the samples were incubated at 95° C. for 60 min. The reaction was stopped by the addition of 0.3 ml of 20% (v/v) trifluoroacetic acid. After the addition of 0.3 ml of 1% (m/v) thiobarbituric acid, the samples were incubated for further 20 min at 95° C. and, after cooling to room temperature, centrifuged. One aliquot was transferred to microphotometric cuvettes, and the absorption was measured at 532 nm.

The inhibition of the lipid peroxidation was calculated according to the following equation:

$$\text{Oxidation inhibition in \%} = (1 - (A_s/A_c)) \cdot 100,$$

wherein $A_s$ is the adsorption of the sample, and $A_c$ is the absorption of the control.

The results are illustrated in FIG. 5. On the y-axis, the oxidation inhibition of the respective polymers is plotted in %. The values shown are the mean values from 3 test repetitions+standard deviation. From these studies it is clearly apparent that on account of their radical-scavenging, complexing and, thus, antioxidant properties, the thiol-group-containing polymers are capable of significantly reducing the oxidation of lipids caused by inflammatory processes.

Example 3

Intradermal Application of the Thiol-Group-Containing Polymers According to the Present Invention The following preparation for intradermal applications was produced: 2 g thiol-group-containing hyaluronic acid was solved in sterile isotone phosphate buffer, stirred to form a partially crosslinked polymer, filled into syringes and sterilised. 0.1 ml of this formulation was injected intradermally into the back region of rabbits. The application produced a minimal local irritation which disappeared after one day. The depot formed by the thiol-group containing hyaluronic acid was tactually detectable over the whole examination period of two weeks.

Example 4

Production of a Preparation for the Subcutaneous and Intradermal Use for Dermal Augmentation A preparation for the subcutaneous and intradermal use was manufactured as follows: 1 g sterile thiol-group containing hyaluronic acid was solved under aseptic conditions and in the absence of oxygen in a 100 ml sterile phosphate buffer pH 7.4. The osmality of this preparation was adjusted by the addition of NaCl to give an osmality of the solution between 200 and 400 mosmol/kg. The solution was filled into flasks and packed gas impermeable.

Example 5

Formulation for Augmenting of Scar Tissue

A preparation was produced as follows: 3 g sterile thiol-group containing hyaluronic acid was solved under aseptic conditions in 100 ml sterile phosphate buffer pH 7.4 and partially crosslinked. Afterwards, the osmality for suggested addition of NaCl to give an osmality of the solution between 200 and 400 mosmol/kg. The solution was filled into flasks and closed gas impermeable.

Example 6

Formulation for Augmenting the Anal and Urethral Sphincter Muscles

The thiol-group containing polymers have been used to augment the internal anal sphincter in order to prevent anal incontinence by supporting natural occurring cushioning in the anal canal. The same formulation was used also to augment the urethral sphincter muscles (see also U.S. Pat. No. 5,785,642). Incontinence is a often occurring problem, in particular for women, whose pelvic floor is significantly weakened after pregnancy. If the pelvic floor muscles cannot be forced by conventional methods, the injection of materials for augmentation of the urethra is a good alternative.

A formulation for the augmentation of the sphincter was produced as follows: 5 g sterile thiol-group-containing chitosan was solved under aseptic conditions in 100 ml sterile borate buffer pH 6.5 and partially crosslinked, the osmality was adjusted by addition of NaCl to 200 to 400 mosmol/kg. The solution was filled into syringes.

Example 7

Enzymatic Degradation of a Single Phase Crosslinked Thiol-Group-Containing Hyaluronic Acid Formulation and a Crosslinked Hyaluronic Acid Particle Comprising Formulation Further advantageous of the thiol-group-containing polymers, in particular of thiol-group-containing hyaluronic acid, is shown in this example. Thiol-group-containing hyaluronic acid and commercially available formulations comprising crosslinked hyaluronic acid particles have been digested with hyaluronidase. In both cases the hyaluronic acid was degraded, whereby the degradation was comparable with an unmodified hyaluronic acid in the case of thiol-group-containing hyaluronic acid and the fragments formed show a much higher molecular weight as the crosslinked hyaluron acid comprising particles. This results from the fact that the disulfide bridges are not degraded by an enzyme and secondly the degree of crosslinking is much higher than in crosslinked hyaluronic acid particles. Therefore, the crosslinked thiol-group-containing hyaluronic acids according to the present invention stay longer at the side of application than crosslinked hyaluronic acid particles.

The invention claimed is:

1. An implant for dermal, muscle, or connective tissue augmentation comprising a thiol-group-containing polymer, wherein the basis polymer is a polysaccharide; wherein the implant stays for at least two weeks at or in the vicinity of the site of application, and wherein the thiol-groups of the thiol-group-containing polymer are partially involved in crosslinking of the polymers via disulfide bridges and partially are available as free thiol-groups and wherein the implant comprises the thiol-group containing polymer at a concentration of from 0.1 to 20% by weight and wherein the implant is formulated for subcutaneous or intradermal administration.

2. The implant of claim 1, wherein the thiol-group-containing polymer has a molecular mass of at least 10,000 g/mol.

3. The implant of claim 2, wherein the thiol-group-containing polymer has a molecular mass of at least 25,000 g/mol.

4. The implant of claim 3, wherein the thiol-group-containing polymer has a molecular mass of at least 50,000 g/mol.

5. The implant of claim 1, wherein thiol-groups within the polymer form inter- and/or intra-molecular disulfide bonds.

6. The implant of claim 1, wherein the thiol-groups comprise more than 20 µmol/g of polymer.

7. The implant of claim 6, wherein the thiol-groups comprise more than 50 µmol/g of polymer.

8. The implant of claim 7, wherein the thiol-groups comprise more than 100 µmol/g of polymer.

9. The implant of claim 1, wherein the thiol-group-containing polymer is thiol-group-containing hyaluronic acid, thiol-group-containing chitosan, or a combination thereof.

10. The implant of claim 1, wherein the thiol-group of the polymer is derived from cysteine, cysteamine, or N-acetyl-cysteine.

11. The implant of claim 1, wherein the implant is provided as a gel or aqueous preparation.

12. The implant of claim 11, wherein the preparation is a single phase preparation.

13. The implant of claim 1, further comprising chitosan and/or hyaluronic acid.

14. The implant of claim 1, further defined as comprising at least one active substance.

15. The implant of claim 14, wherein the at least one active substance is an antiphlogistic agent, antirheumatic agent, analgesic, anti-infective agent, antiviral agent, antibiotic, antimycotic, antiseptic agent, chemotherapeutic agent, spasmolytic, vitamin, cytostatic agent, local anesthetic, antiallergic agent, antihistamine, anti-inflammatory agent, antivaricosic agent, agent for treating hemorrhoids, therapeutic agent for treating the skin, gynecologic agent, ophthalmic agent, urologic agent, rhinologic agent, or otologic agent.

16. The implant of claim 14, further defined as comprising at least one pharmaceutical excipient.

17. The implant of claim 16, wherein the at least one pharmaceutical excipient is a buffer salt, preserving agent, excipient for adjusting the desired osmolality, excipient for adjusting the desired viscosity, stabilizer, softener, coating material, flow agent, binder, lubricant, filler, desiccant, disintegrating agent, solvent, solubilizer, or excipient for enhancing the compatibility of the formulation.

18. A method for the cosmetic augmentation of the skin comprising:

obtaining an implant of claim 1; and applying the implant subcutaneously and/or intradermally.

19. The method of claim 18, wherein the implant reduces inflammation and/or oxidation of the skin at the site of implantation.

* * * * *